(12) United States Patent
Yamagata et al.

(10) Patent No.: US 11,484,268 B2
(45) Date of Patent: Nov. 1, 2022

(54) BIOLOGICAL SIGNAL ANALYSIS DEVICE, BIOLOGICAL SIGNAL MEASUREMENT SYSTEM, AND COMPUTER-READABLE MEDIUM

(71) Applicants: Hideaki Yamagata, Kanagawa (JP); Eiichi Okumura, Ishikawa (JP); Noriyuki Tomita, Ishikawa (JP)

(72) Inventors: Hideaki Yamagata, Kanagawa (JP); Eiichi Okumura, Ishikawa (JP); Noriyuki Tomita, Ishikawa (JP)

(73) Assignee: RICOH COMPANY, LTD., Tokyo (JP)

( * ) Notice: Subject to any disclaimer, the term of this patent is extended or adjusted under 35 U.S.C. 154(b) by 310 days.

(21) Appl. No.: 16/292,480

(22) Filed: Mar. 5, 2019

(65) Prior Publication Data
US 2019/0282174 A1    Sep. 19, 2019

(30) Foreign Application Priority Data

Mar. 15, 2018  (JP) .............................. JP2018-047468
Dec. 27, 2018  (JP) .............................. JP2018-245889

(51) Int. Cl.
*A61B 5/00*   (2006.01)
*A61B 5/246*  (2021.01)
*A61B 5/377*  (2021.01)

(52) U.S. Cl.
CPC ............ *A61B 5/7203* (2013.01); *A61B 5/246* (2021.01); *A61B 5/377* (2021.01); *A61B 5/4812* (2013.01); *A61B 5/7285* (2013.01); *A61B 5/7425* (2013.01)

(58) Field of Classification Search
CPC ..... A61B 55/7203; A61B 5/246; A61B 5/377; A61B 5/7425; A61B 5/7285; A61B 5/4812; A61B 5/055
See application file for complete search history.

(56) References Cited

U.S. PATENT DOCUMENTS

2003/0032889 A1 *  2/2003  Wells .................. A61B 5/4041
                                                              600/546
2005/0217674 A1    10/2005  Burton et al.
(Continued)

FOREIGN PATENT DOCUMENTS

JP    2001-008915    1/2001
JP       3584286     8/2004
(Continued)

OTHER PUBLICATIONS

Tadel et al, "Brainstorm: A User-Friendly Applicaton for MEG/EEG Analysis", vol. 2011.Computational Intelligence and Neuroscience, p. 1-13 (Year: 2011).*

(Continued)

*Primary Examiner* — Gary Jackson
*Assistant Examiner* — Sebastian X Lukjan
(74) *Attorney, Agent, or Firm* — Harness, Dickey & Pierce, P.L.C.

(57) ABSTRACT

A biological signal analysis device includes: an acquiring unit configured to acquire biological signals of a measurement target; a trigger information acquiring unit configured to acquire, from a stimulator configured to apply stimuli to the measurement target, trigger information indicating times at which the stimuli are generated; and a signal processing unit configured to process the biological signals. The signal processing unit is configured to calculate biological information on the measurement target based on the biological signals, maintain only pieces of trigger information corresponding to times at which it is determined that biological signals of the measurement target are generated, from the calculated biological information, delete another piece of trigger information, and use an averaged waveform that is obtained by performing an averaging process on the bio- (Continued)

logical signals that are generated in synchronization with the stimuli based on the pieces of remaining trigger information.

18 Claims, 12 Drawing Sheets

(56) References Cited

U.S. PATENT DOCUMENTS

| | | | |
|---|---|---|---|
| 2007/0118054 A1 | 5/2007 | Pinhas et al. | |
| 2011/0192400 A9 | 8/2011 | Burton et al. | |
| 2012/0125337 A1 | 5/2012 | Asanoi | |
| 2012/0130205 A1 | 5/2012 | Burton et al. | |
| 2012/0132202 A1 | 5/2012 | Burton et al. | |
| 2012/0136405 A1 | 5/2012 | Burton et al. | |
| 2013/0109996 A1* | 5/2013 | Turnbull | A61B 5/7264 600/544 |
| 2013/0218043 A1* | 8/2013 | Yoshida | A61B 5/316 600/544 |
| 2013/0245502 A1 | 9/2013 | Lange et al. | |
| 2014/0333529 A1* | 11/2014 | Kim | G06F 3/015 345/156 |
| 2015/0302722 A1* | 10/2015 | Berezhnyy | A61B 5/6892 340/565 |
| 2019/0129606 A1 | 5/2019 | Shinohara et al. | |

FOREIGN PATENT DOCUMENTS

| | | |
|---|---|---|
| JP | 2005-131122 | 5/2005 |
| JP | 4865229 | 11/2011 |
| JP | 5089676 | 9/2012 |
| JP | 5273758 | 5/2013 |
| JP | 2013-154190 | 8/2013 |
| JP | 5679971 | 1/2015 |
| JP | 2016-087072 | 5/2016 |
| JP | 2019-80896 A | 5/2019 |

OTHER PUBLICATIONS

Tutorial 13: Artifact cleaning with SSP [online], brainstorm USC univeristy using wayback machine [retrieved on Feb. 21, 2019] Retrieved from the Internet: <https://web.archive.org/web/20160823032922/http://neuroimage.usc.edu/brainstorm/Tutorials/ArtifactsSsp> (Year: 2016).*

Scanning and displaying dipoles [online],brainstorm USC univeristy using wayback machine [retrieved on Aug. 20, 2021] Retrieved from the Internet: <https://web.archive.org/web/20160822031820/http://neuroimage.usc.edu/brainstorm/Tutorials/TutDipScan> (Year: 2016).*

Rie Sakurada, et al. "High frequency oscillations are less frequent but more specific to epileptogenicity during rapid eye movement sleep" Clinical Neurophysiology 127 (2016) 179-186.

Keita Tanaka, et al. "Modulation of Steady-State Visually Evoked Fields by Emotions" revised Jul. 2, 2013. 285-291.

Norio Fujimaki, et al. "3-6 Neural Activation Related to Language Processes and an Analysis Method" vol. 50 Nos. 3/4 2004.

U.S. Appl. No. 16/133,821, filed Sep. 18, 2018.

* cited by examiner

FIG.13

<SLEEP STAGE>

| SLEEP STAGE | INTERNATIONAL CLASSIFICATION DETERMINATION STANDARD | |
|---|---|---|
| StageW<br>WAKEFULNESS | ・α WAVES, LOW-VOLTAGE WAVES<br>・RAPID EYE MOVEMENTS, HIGH-VOLTAGE ELECTROMYOGRAPHY | |
| Stage I<br>RELAXED WAKEFULNESS | ・α WAVES ≤ 50%, LOW-VOLTAGE WAVES OF VARIOUS FREQUENCIES ARE MIXED, HUMP<br>・SLOW EYE MOVEMENTS, SLIGHTLY-DECREASED MUSCLE TONE | NON-REM SLEEP |
| Stage II<br>LIGHT SLEEP | ・LOW-VOLTAGE IRREGULAR THETA WAVES TO DELTA WAVES, NO HIGH-VOLTAGE SLOW WAVE<br>・HUMP, SPINDLE WAVES, K-COMPLEX | NON-REM SLEEP |
| Stage III<br>SLOW-WAVE SLEEP | ・SLOW WAVES IN RANGE OF 2 Hz TO 75 μV: 20-50%<br>・SPINDLE WAVES WITH DECREASED FREQUENCIES APPEAR IN WIDE RANGE | NON-REM SLEEP |
| Stage IV<br>DEEP SLEEP | ・SLOW WAVES IN RANGE OF 2 Hz TO 75 μV: 50% OR MORE<br>・SPINDLE WAVES (±) | NON-REM SLEEP |
| StageREM<br>REM SLEEP | ・SAME AS STAGE I, NO HUMP<br>・RAPID EYE MOVEMENTS, APPARENTLY-DECREASED MUSCLE TONE | REM SLEEP |

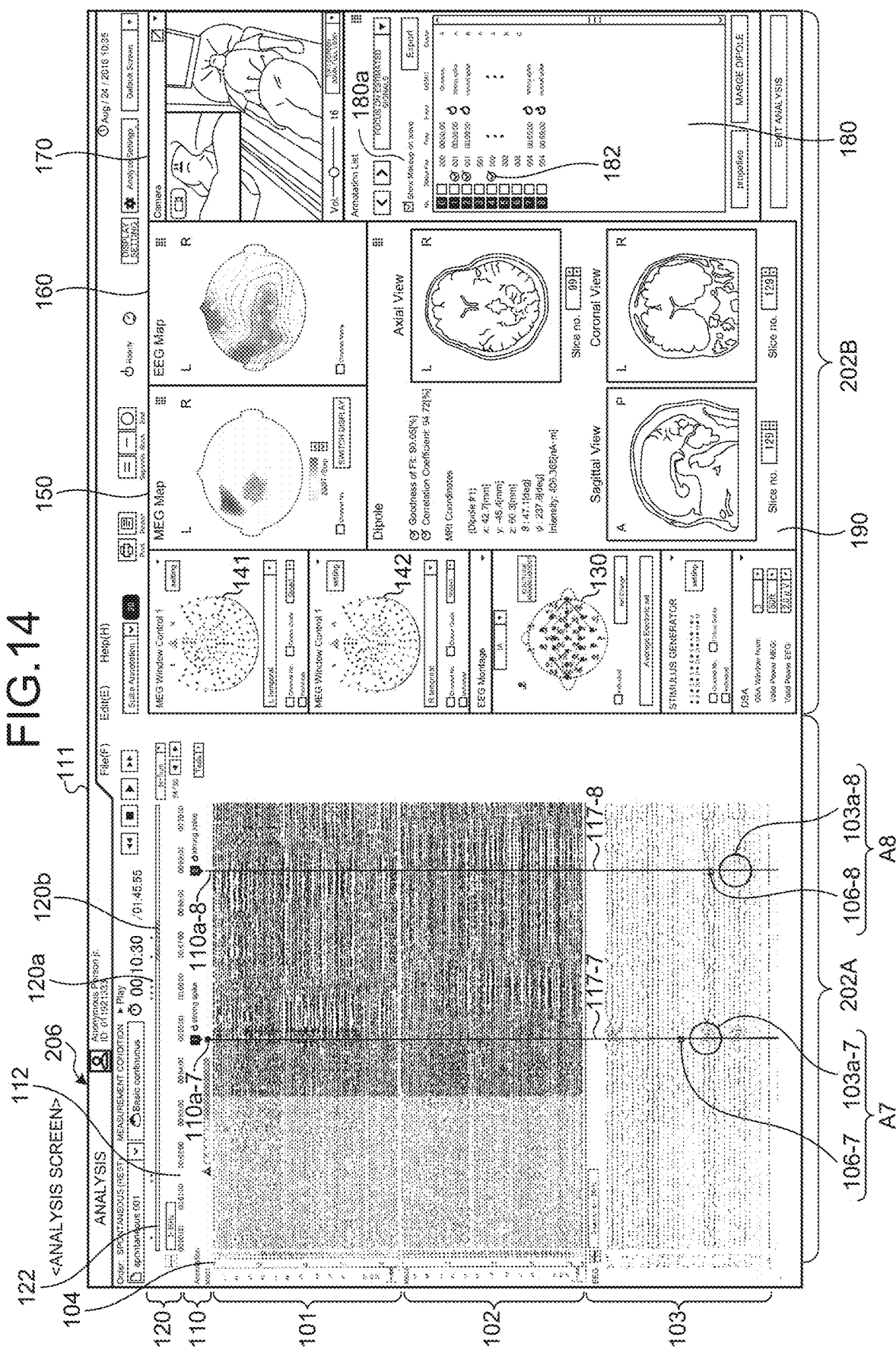

BIOLOGICAL SIGNAL ANALYSIS DEVICE, BIOLOGICAL SIGNAL MEASUREMENT SYSTEM, AND COMPUTER-READABLE MEDIUM

CROSS-REFERENCE TO RELATED APPLICATIONS

The present application claims priority under 35 U.S.C. § 119 to Japanese Patent Application No. 2018-047468, filed on Mar. 15, 2018 and Japanese Patent Application No. 2018-245889 filed in Japan on Dec. 27, 2018. The contents of which are incorporated herein by reference in their entirety.

BACKGROUND OF THE INVENTION

1. Field of the Invention

The present invention relates to a biological signal analysis device, a biological signal measurement system, and a computer-readable medium.

2. Description of the Related Art

Conventionally, a technique for measuring brain activity (functional brain mapping) to identify positions of the visual cortex, the auditory cortex, the somatosensory association cortex, the motor cortex, and the speech area by applying some kinds of stimuli to a to-be-measured person who is a measurement target has been known.

To measure the brain activity as described above, various measurement devices are used. For example, a measurement device that measures biological signals of a magnetoencephalography (MEG), an electroencephalography (EEG), functional magnetic resonance imaging (fMRI), and the like is mainly used.

Japanese Patent No. 3584286 discloses a technique for giving feedback, based on visual stimuli, on a gap between activity of a to-be-measured person who is a measurement target and the stimuli to the to-be-measured person for whom the motor cortex is to be identified, in order to maintain and stimulate motivation and concentration of the to-be-measured person during measurement of the brain activity.

According to the conventional technique, a task of "pressing a button" is also imposed in order to check whether the brain activity (brain reaction to stimuli) certainly occurs, in addition to viewing the visual stimuli during examination of the visual cortex.

However, the task of "pressing a button" itself evokes brain activity. Therefore, when only reaction to the visual stimuli is to be checked, the brain activity that occurs due to the task of "pressing a button" may become noise.

In contrast, if the task of "pressing a button" or the like is not imposed, it is difficult to recognize a situation in which the to-be-measured person is not awake (for example, the to-be-measured person falls asleep). If the to-be-measured person falls asleep, it is difficult to assume that the brain activity against stimuli is measured with accuracy.

SUMMARY OF THE INVENTION

According to an aspect of the present invention, a biological signal analysis device includes an acquiring unit, a trigger information acquiring unit, and a signal processing unit. The acquiring unit is configured to acquire biological signals of a measurement target from a biological signal measurement device configured to measure the biological signals. The trigger information acquiring unit configured to acquire, from a stimulator configured to apply stimuli to the measurement target, trigger information indicating times at which the stimuli are generated. The signal processing unit is configured to process the biological signals. The signal processing unit is configured to calculate biological information on the measurement target based on the biological signals, maintain only pieces of trigger information corresponding to times at which it is determined that biological signals of the measurement target are generated, from the calculated biological information, delete another piece of trigger information, and use an averaged waveform that is obtained by performing an averaging process on the biological signals that are generated in synchronization with the stimuli based on the pieces of remaining trigger information.

BRIEF DESCRIPTION OF THE DRAWINGS

FIG. 13 is a diagram illustrating standard sleep stages; and

FIG. 14 is a diagram illustrating another example of the analysis screen.

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
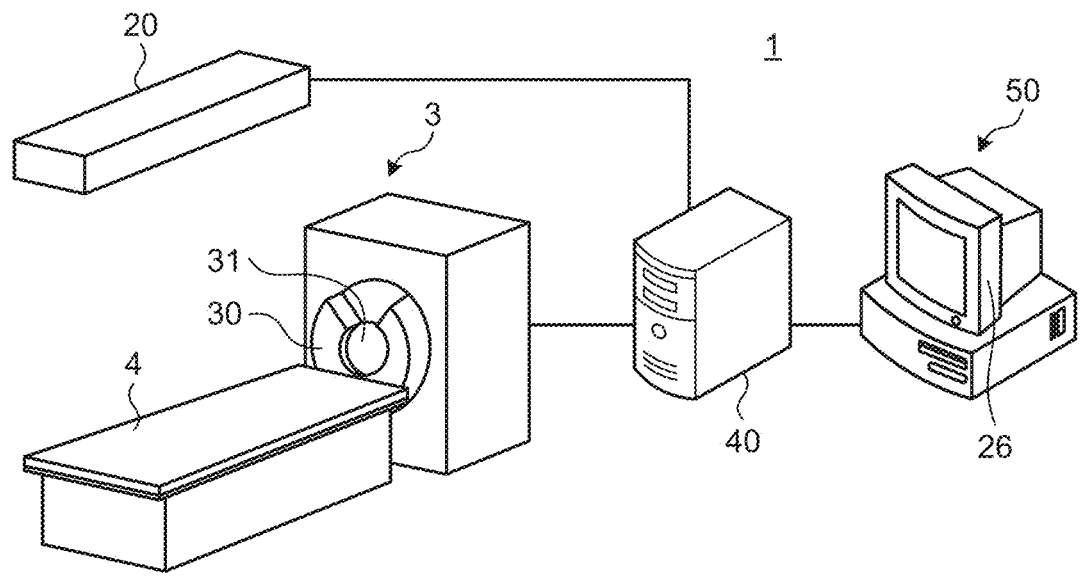
FIG. 1 is a schematic diagram of a biological signal measurement system according to an embodiment.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

An embodiment has an object to improve analysis accuracy.

Exemplary embodiments of a biological signal analysis device, a biological signal measurement system, and a computer-readable medium will be described in detail below with reference to the drawings.

FIG. 1 is a schematic diagram of a biological signal measurement system 1 according to an embodiment. As illustrated in FIG. 1, the biological signal measurement system 1 measures and displays a plurality of kinds of biological signals, such as a magnetoencephalography (MEG) signal and an electroencephalography (EEG) signal, of a to-be-measured person who is a measurement target. The biological signals to be measured are not limited to the magnetoencephalography signal and the electroencephalography signal, but may be, for example, an electrical signal that is generated in accordance with activity of heart (electrical signal that can be represented on an electrocardiogram).

As illustrated in FIG. 1, the biological signal measurement system 1 includes a measurement device 3 that is a biological signal measurement device that measures one or more biological signals of the to-be-measured person, a server 40 that records the one or more biological signals measured by the measurement device 3, a stimulator 20 that applies one or more stimuli to a subject, and an information processing apparatus 50 that is a biological signal analysis device that analyzes the one or more biological signals recorded in the server 40. In this example, the server 40 and the information processing apparatus 50 are described as separate devices, but at least a part of functions of the server 40 may be incorporated in the information processing apparatus 50, for example.

In the example in FIG. 1, the subject (to-be-measured person) lies on his/her back on a measurement table 4 while wearing electrodes (or sensors) for electroencephalography measurement on his/her head, and puts the head into a hollow 31 of a dewar 30 of the measurement device 3. The dewar 30 is a container in a cryogenic environment using liquid helium, and a number of magnetic sensors for magnetoencephalography measurement are arranged inside the hollow 31 of the dewar 30. The measurement device 3 collects electroencephalography signals from the electrodes and magnetoencephalography signals from the magnetic sensors and outputs data including the electroencephalography signals and the magnetoencephalography signals thus collected (hereinafter, may be referred to as "measurement data" in some cases) to the server 40. The measurement data recorded in the server 40 is read and displayed by the information processing apparatus 50 and then analyzed. In general, the dewar 30 with the built-in magnetic sensors and the measurement table 4 are arranged in a magnetic shielding room, but the magnetic shielding room is not illustrated for convenience of illustration.

The stimulator 20 generates stimuli that are programmed in advance and simultaneously outputs data including trigger signals indicating times at which the stimuli are generated to the server 40.

The stimulator 20 may be, for example, an electrode arranged on a belt, or the like. In this case, for example, the stimulator 20 is attached to an arm or the like of the to-be-measured person, and applies electrical signals or mechanical signals as stimuli to the to-be-measured person.

Further, the stimulator 20 may be, for example, a display device, an audio output device, or the like. In this case, for example, the stimulator 20 provides video displayed on the stimulator 20, audio output from the stimulator 20, or the like as stimuli to the to-be-measured person. In this manner, the stimulator 20 is able to apply various stimuli that are determined by a measurement procedure to the to-be-measured person.

The information processing apparatus 50 displays waveforms of the magnetoencephalography signals obtained from the plurality of magnetic sensors and waveforms of the electroencephalography signals obtained from the plurality of electrodes on the same time axis in a synchronous manner. At the same time, it may be possible to display triggers in a synchronous manner. The electroencephalography signals are signals that represent electrical activity of nerve cells (the flow of ionic charge that occurs in neuronal dendrites during synapse transmission) by voltage values between the electrodes. The magnetoencephalography signals are signals that represent fine magnetic field variation that occurs due to electrical activity of the brain. The brain's magnetic field is detected by a high-sensitive superconducting quantum interference device (SQUID) sensor. The electroencephalography signals and the magnetoencephalography signals are one example of a "biological signal".

Figure 2:
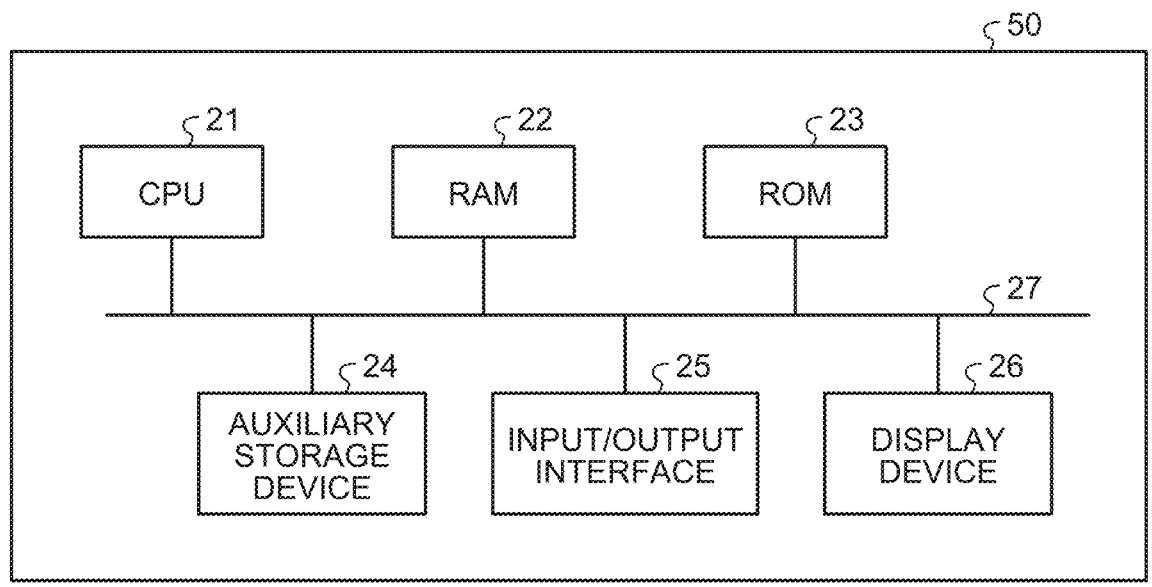
FIG. 2 is a hardware configuration diagram of an information processing apparatus.

FIG. 2 is a hardware configuration diagram of the information processing apparatus 50. The information processing apparatus 50 includes a central processing unit (CPU) (processor) 21, a random access memory (RAM) 22, a read only memory (ROM) 23, an auxiliary storage device 24, an input/output interface 25, and a display device 26, all of which are connected to one another via a bus 27.

The CPU 21 controls entire operation of the information processing apparatus 50 and performs various kinds of information processing. The CPU 21 executes information display program that is stored in the ROM 23 or the auxiliary storage device 24 and controls operation of displaying a measurement recording screen and an analysis screen. The RAM 22 is used as a working area for the CPU 21, and may include a non-volatile RAM for storing main control parameters and information. The ROM 23 stores therein a basic input/output program and the like. The information display program of embodiments may be stored in the ROM 23. The auxiliary storage device 24 is a storage device, such as a solid state drive (SSD) or a hard disk drive (HDD), and stores therein, for example, a control program for controlling operation of the information processing apparatus 50, various kinds of data needed for the operation of the information processing apparatus 50, files, and the like. The input/output interface 25 includes both of a user interface, such as a touch panel, a keyboard, a display screen, and an operation button, and a communication interface for loading information from various sensors or the server 40 and outputting analysis information to other electronic devices. The display device 26 is a device (display) for displaying various kinds of information. The display device 26 displays the measurement recording screen and the analysis screen, and the screens are updated in accordance with input-output operation that is performed via the input/output interface 25.

Figure 3:
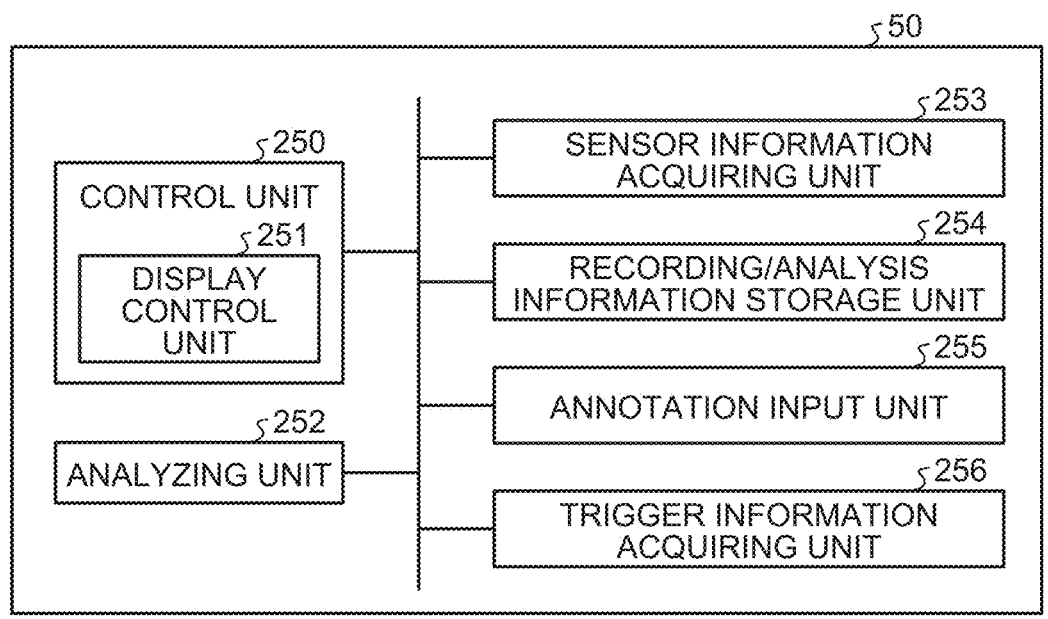
FIG. 3 is a functional block diagram of the information processing apparatus.

FIG. 3 is a functional block diagram of the information processing apparatus 50. The information processing apparatus 50 includes a control unit 250, an analyzing unit 252 serving as a signal processing means, a sensor information acquiring unit 253 serving as an acquiring means, a trigger information acquiring unit 256 serving as a trigger information acquiring means, a recording/analysis information storage unit 254, and an annotation input unit 255 serving as an annotation input means. The control unit 250 includes a display control unit 251 serving as a display control means that controls display of screens in the information processing apparatus 50.

The sensor information acquiring unit 253 acquires sensor information (biological signal) from the measurement device 3 or the server 40.

The trigger information acquiring unit 256 acquires trigger information from the measurement device 3 or the server 40.

The annotation input unit 255 inputs annotation information to be added to the sensor information.

The analyzing unit 252 analyzes the collected sensor information. Analysis of the sensor information includes averaging of signal waveforms, analysis of signal waveforms including an averaged waveform, analysis of a singularity of amplitude, analysis of the brain's magnetic field including orientation of a current dipole, and the like. In other words, in this example, the analyzing unit 252 has a function to estimate a signal source corresponding to an annotation that is selected from the analysis screen (a function of an estimating unit).

The display control unit 251 controls display of screens at the time of measurement and recording of the sensor information and at the time of analysis.

The recording/analysis information storage unit 254 stores therein measurement data and analysis results. When an annotation is added to a signal waveform at the time of measurement and recording, the annotation is also stored in association with time information indicating an acquisition time of the signal waveform.

The functions of the control unit 250 including the display control unit 251 are implemented by causing the CPU 21 illustrated in FIG. 2 to read a program stored in the ROM 23 or the like, loads the program onto the RAM 22, and executes the program. Similarly, the functions of the analyzing unit 252 are implemented by causing the CPU 21 illustrated in FIG. 2 to read a program stored in the ROM 23 or the like, loads the program onto the RAM 22, and executes the program. Meanwhile, embodiments are not limited to this example, and, for example, a part or all of the functions of the control unit 250 and the analyzing unit 252 may be implemented by a dedicated hardware circuit (semiconductor integrated circuit or the like). The functions of the sensor information acquiring unit 253 and the annotation input unit 255 are implemented by the input/output interface 25. The functions of the recording/analysis information storage unit 254 are implemented by the ROM 23 or the auxiliary storage device 24.

Figure 4:
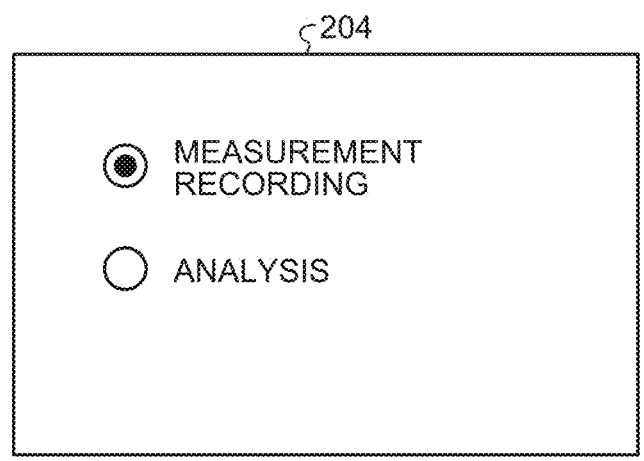
FIG. 4 is a diagram illustrating an example of a start screen displayed on the information processing apparatus.

FIG. 4 is a diagram illustrating an example of a start screen 204 displayed by the information processing apparatus 50. The start screen 204 displays selection boxes for "measurement/recording" and "analysis". In electroencephalography and/or magnetoencephalography measurement, it is often the case that data measurement/recording and data analysis are performed by different entities. For example, when a measurement technician (measurer) selects the box of "measurement/recording", pieces of data measured by the measurement device 3 are sequentially stored in the server 40 and then read and displayed by the information processing apparatus 50. When a doctor selects the box of "analysis" after measurement and recording are completed, the recorded measurement data are read and analyzed.

Operation at the Time of Measurement/Recording

Figure 5:
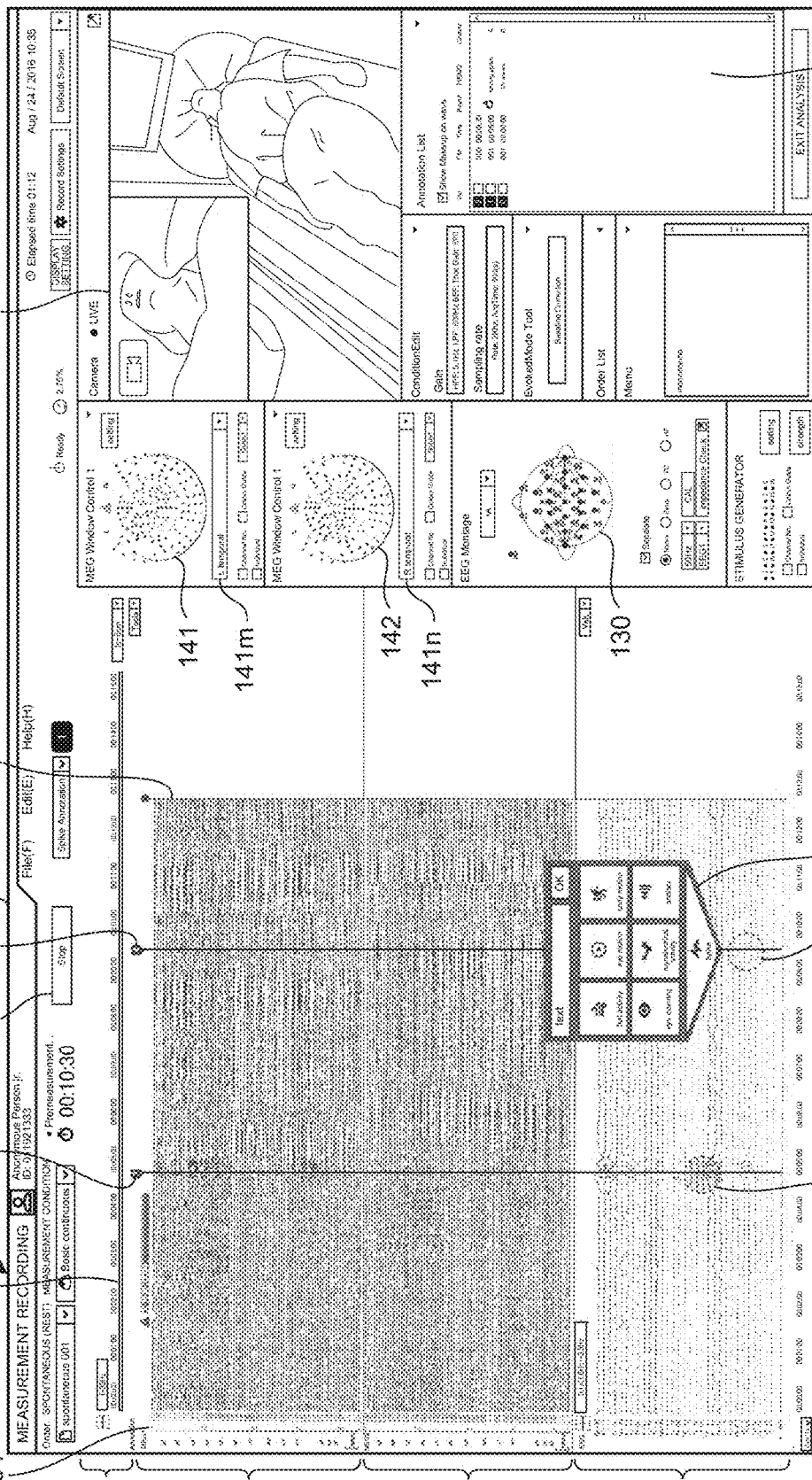
FIG. 5 is a diagram illustrating an example of a measurement recording screen.

FIG. 5 is a diagram illustrating an example of a measurement recording screen 205. The measurement recording screen 205 includes a region 201A for displaying measured signal waveforms and a region 201B for displaying monitor information other than the signal waveforms. The region 201A for displaying the signal waveforms is arranged on the left side of the screen when viewed from the measurer's side, and the region 201B for displaying monitor information other than the signal waveforms is arranged on the right side of the screen when viewed from the measurer's side. This configuration prevents unnecessary movement of the line of sight of the measurer along with movement of a waveform that is detected and displayed in real time (displayed from the left side to the right side on the screen) and unnecessary movement of a mouse from the left-side region 201A to the right-side region 201B of the screen, so that it is possible to improve operation efficiency.

A monitor window 170 for checking the condition of a to-be-measured person during measurement is displayed in the region 201B of the display screen.

The region 201A includes a first display region 110 for displaying time information on signal detection in a horizontal direction (first direction) of the screen, and waveform display regions 101 to 103 for displaying a plurality of signal waveforms, which are based on the signal detection, in parallel in a vertical direction (second direction) of the screen.

The time information displayed in the first display region 110 is a timeline including time display that is added along a time axis 112, but it may be possible to display only a stripe-shaped axis without displaying time (number) or it may be possible to display only time (number) without arranging the axis. Further, it may be possible to display a time axis to display a timeline below the waveform display region 103, in addition to the first display region 110 that is arranged on the upper side of the screen.

The region 201A displays a plurality of signal waveforms that are acquired from a plurality of sensors of the same kind or a plurality of kinds of signal waveforms that are acquired from a plurality of kinds of sensors, in a synchronous manner on the same time axis. For example, waveforms of a plurality of magnetoencephalography signals that are obtained from the right side of the head of the to-be-measured person are displayed in parallel in the waveform display region 101, and waveforms of a plurality of magnetoencephalography signals that are obtained from the left side of the head of the to-be-measured person are displayed in parallel in the waveform display region 102. Waveforms of a plurality of electroencephalography signals are displayed in parallel in the waveform display region 103. The plurality of electroencephalography signal waveforms are voltage signals that are measured among a plurality of electrodes. Each of the signal waveforms is displayed at a channel axis 104, in association with an identification number or a channel number of a sensor that has acquired the signal.

When measurement is started and measurement information is collected from each of the sensors, signal waveforms are displayed rightward from the left edge of each of the waveform display regions 101 to 103 in the region 201A with time. A line 113 indicates a measurement time (current time) and moves from left to right in the screen. When a signal waveform is displayed up to the right edge of the region 201A (the right edge of the time axis 112), the signal waveform is gradually deleted from the left edge to the right side of the screen, and a new signal waveform is sequentially displayed form left to right in the deleted position and the line 113 moves rightward from the left edge. Along with this operation, a lapse of time is displayed on the time axis 112 in the first display region 110 in the horizontal direction in accordance with the progress of the measurement. The measurement and recording are continued until a termination button 119 is pressed.

As a feature of the embodiment, when a measurer (recording person) finds waveform disturbance on a signal waveform, a singularity of amplitude, or the like during data recording, it is possible to mark a problematic portion or range on the signal waveform. The portion or the range to be marked can be specified by pointer operation or click operation using a mouse. The specified portion (or range) is displayed with emphasis on the signal waveforms in the waveform display regions 101 to 103, and a temporal position or a time range corresponding to a specification result is displayed along the time axis 112 in the first display region 110. Information on the marking including the display on the time axis 112 is stored together with signal waveform data. The specified portion corresponds to a certain time, and the specified range corresponds to a certain range including a certain time.

In the example in FIG. 5, a range including one or more channels is specified at a time t1 in the waveform display region 103, and a mark 103a-1 representing a time period including the time t1 is displayed in a highlighted manner. An annotation 110a-1 indicating a specification result is displayed at a corresponding temporal position in the first display region 110 in association with the display of the mark 103a-1. At a time t2, a different waveform position or a neighboring position of the different waveform position is marked in the waveform display region 103, and a mark 103a-2 is displayed in a highlighted manner at this position (the time t2) or a neighboring region (at least a time range or any one of the waveforms is specified). At the same time, an annotation 110a-2 is displayed at a corresponding temporal position (time range) in t the first display region 110. Here, the annotation indicates that related information is added as an annotation to certain data. In the present embodiment, the annotation is displayed based on at least the specified time information and is displayed in association with at least a position at which a waveform based on the time information is displayed. Further, when a plurality of channels are displayed, annotations may be displayed in association with corresponding channel information.

If the measurer specifies a different waveform portion or a neighboring region of the different waveform portion at the time t2, the mark 103a-2 is displayed in a highlighted manner in the specified portion, and an annotation number of "2" is simultaneously displayed at a corresponding temporal position in the first display region 110. Furthermore, a pop-up window 115 for selecting an attribute is displayed in the portion that is displayed in a highlighted manner. The pop-up window 115 includes selection buttons for selecting various attributes, and an input box for inputting comments and additional information. The selection buttons indicate, as attributes of a waveform, causes of waveform disturbance, such as "fast activity", "eye motion", "body motion", and "spike". The measurer is able to check the condition of the to-be-measured person using the monitor window 170 in the region 201B of the screen, and therefore is able to appropriately select an attribute indicating a cause of waveform disturbance. For example, when a spike occurs in a waveform, it is possible to determine whether the spike indicates a symptom of epilepsy or the spike is caused by body motion (sneeze or the like).

A part or all of the annotation 110a-1, e.g., at least one of the attribute icon and the text annotation, may also be displayed near the mark 103a-1 on the signal waveform in the waveform display region 103. Adding an annotation on a signal waveform may cause interference with checking of a waveform shape; therefore, when displaying an annotation on the signal waveforms in the waveform display regions 101 to 103, it is preferable to allow selection of display or non-display of the annotation.

The monitor window 170 in the region 201B displays a live video of the condition of the to-be-measured person who is lying down on the measurement table 4 with his/her head in the measurement device 3. In the region 201B, distribution maps 141, 142, and 130 corresponding to the respective signal waveforms in the waveform display regions 101, 102, and 103 and an annotation list 180 are displayed.

The magnetoencephalography distribution maps 141 and 142 are magnetoencephalography distribution maps that indicate arrangement of magnetic sensors for magnetoencephalography measurement. The magnetic sensors are represented by points arranged in the magnetoencephalography distribution maps 141 and 142. The electroencephalography distribution map 130 is an electroencephalography distribution map that indicates arrangement of electrodes (or sensors) for electroencephalography measurement.

To perform measurement and recording, the measurer specifies, in the magnetoencephalography distribution maps 141 and 142, magnetic sensors corresponding to waveforms to be displayed in the waveform display regions 101 and 102.

As one example of a method of specifying the magnetic sensors, the measurer may specify the magnetic sensors from pull-down lists that are displayed by pressing menus 141m and 141n. For example, the pull-down list displays not only selections of left and right sensor groups but also some parts, such as a parietal region, a frontal lobe, and a temporal lobe, and it is possible to arbitrarily select sensors. For example, when a sensor corresponding to the parietal region in the magnetoencephalography distribution map 141 is selected using the menu 141m, all of sensors other than the sensors corresponding to the parietal region in the magnetoencephalography distribution map 142 are selected using the menu 141n. Then, when magnetic sensors are specified, colors of corresponding points in the magnetoencephalography distribution maps 141 and 142 are distinguished from those of points that are not specified.

Further, the identification numbers or the channel numbers of the sensors displayed on the channel axis 104 are numbers assigned to the sensors corresponding to the parietal region in the waveform display region 101, and are numbers assigned to the other sensors in the waveform display region 102.

As another example of the method of specifying the magnetic sensors, a measurer or an analyzer may enclose magnetic sensors (represented by points) to be specified in the magnetoencephalography distribution maps 141 and 142 by using an operation means, such as a mouse. In this case, colors of points (magnetic sensors) inside the enclosed area are distinguished from those of points that are located outside the area.

The annotation list 180 is a list of annotations that are marked on the signal waveforms in the region 201A. Every time a certain position or range is specified on the signal waveforms in the waveform display regions 101 to 103 and an annotation is added, corresponding information is sequentially added to the annotation list 180.

If the termination button 119 is selected (pressed) and measurement is terminated, the highlighted portions specified in the waveform display regions 101 to 103 are stored in association with the signal waveforms. The annotation information that is displayed at the corresponding temporal position in the first display region 110 is also stored in association with the annotation number and the time. By storing the display information as described above, an analyzer can easily recognize and analyze a problematic portion even when the analyzer and the measurer are different persons.

Figure 6:
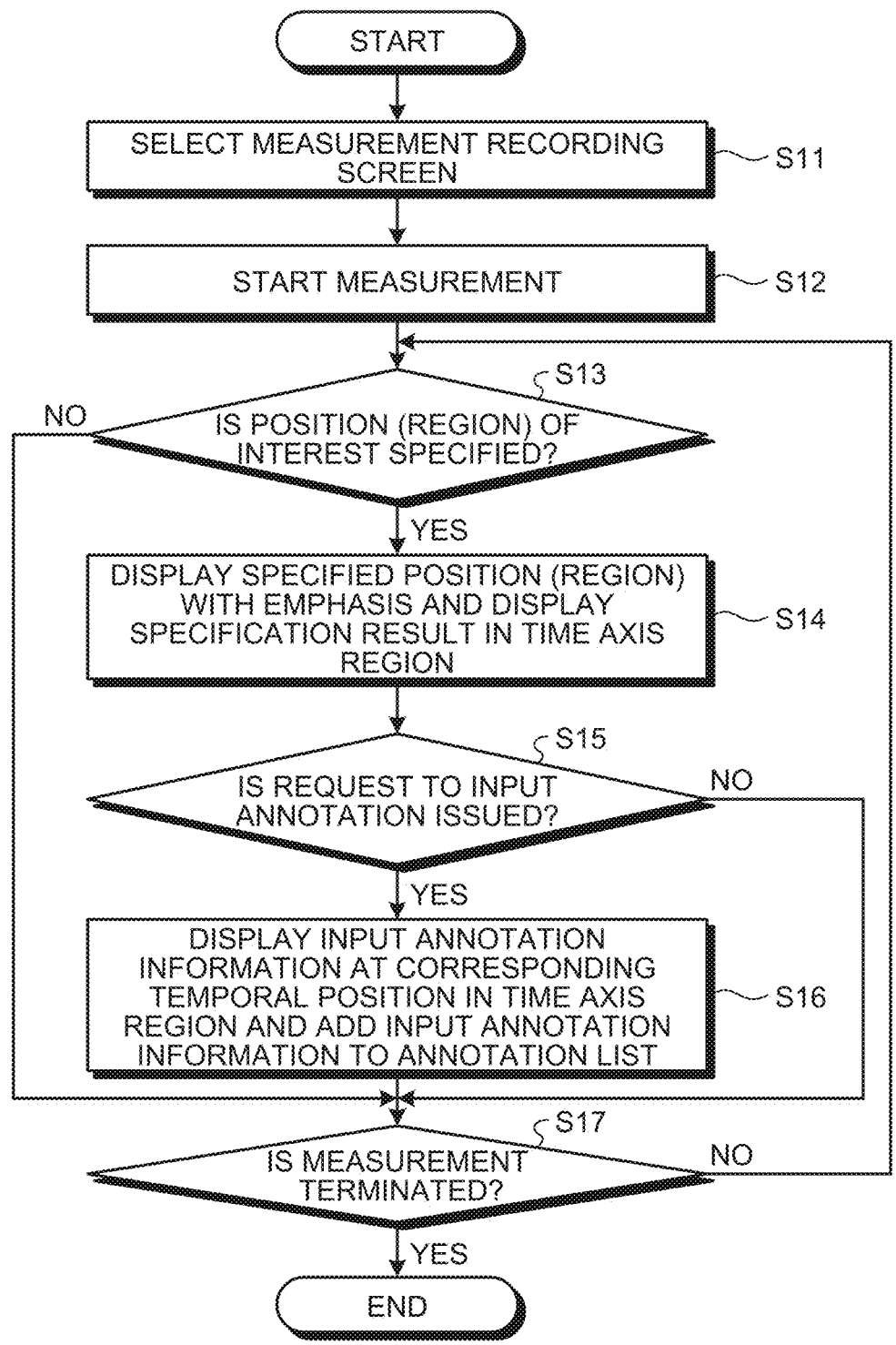
FIG. 6 is a flowchart illustrating operation that is performed by the information processing apparatus at the time of measurement and recording.

FIG. 6 is a flowchart illustrating operation that is performed by the information processing apparatus 50 at the time of measurement and recording. If "measurement recording" is selected in the start screen 204 illustrated in FIG. 4 (S11), measurement is started, and waveforms of a plurality of signals are displayed in a synchronous manner along the same time axis (S12). Here, "a plurality of signal waveforms" includes both of a plurality of signal waveforms that are detected by a plurality of sensors of the same kind and a plurality of signal waveforms that are detected by a plurality of kinds of sensors. In this example, waveforms of a plurality of biological signals include waveforms of magnetoencephalography signals that are obtained from a group of magnetic sensors corresponding to the right side of the head of the to-be-measured person, waveforms of magnetoencephalography signals that are obtained from a group of magnetic sensors corresponding to the left side of the head of the to-be-measured person, waveforms of electroencephalography signals that are obtained from electrodes for electroencephalography measurement on the to-be-measured person, but embodiments are not limited to this example.

The information processing apparatus 50 determines whether a portion or range of interest is specified on the displayed signal waveforms (S13). If the portion or range of interest is specified (YES at Step S13), the specified portion is displayed with emphasis in the display regions (the waveform display regions 101 to 103) of the signal waveforms, and a specification result is displayed at a corresponding temporal position in the time axis region (the first display region 110) (S14). The specification result includes information indicating that specification is performed or information for identifying the specification. At the same time, before, or after the specification result is displayed in the time axis region, it is determined whether a request to input an annotation is issued (S15). If the request to input an annotation is issued (YES at Step S15), input annotation information is displayed at a corresponding temporal position in the time axis region and is added to the annotation list 180 (S16). Thereafter, it is determined whether a measurement termination command is input (S17). If a position (region) of interest is not specified (NO at Step S13) or if the request to input an annotation is absent (NO at Step S15), the process proceeds to Step S17 and it is determined whether to terminate the measurement. The processes from Step S13 to S16 are repeated (NO at Step S17) until the measurement is terminated (YES at Step S17).

Operation at the Time of Analysis

Figure 7:
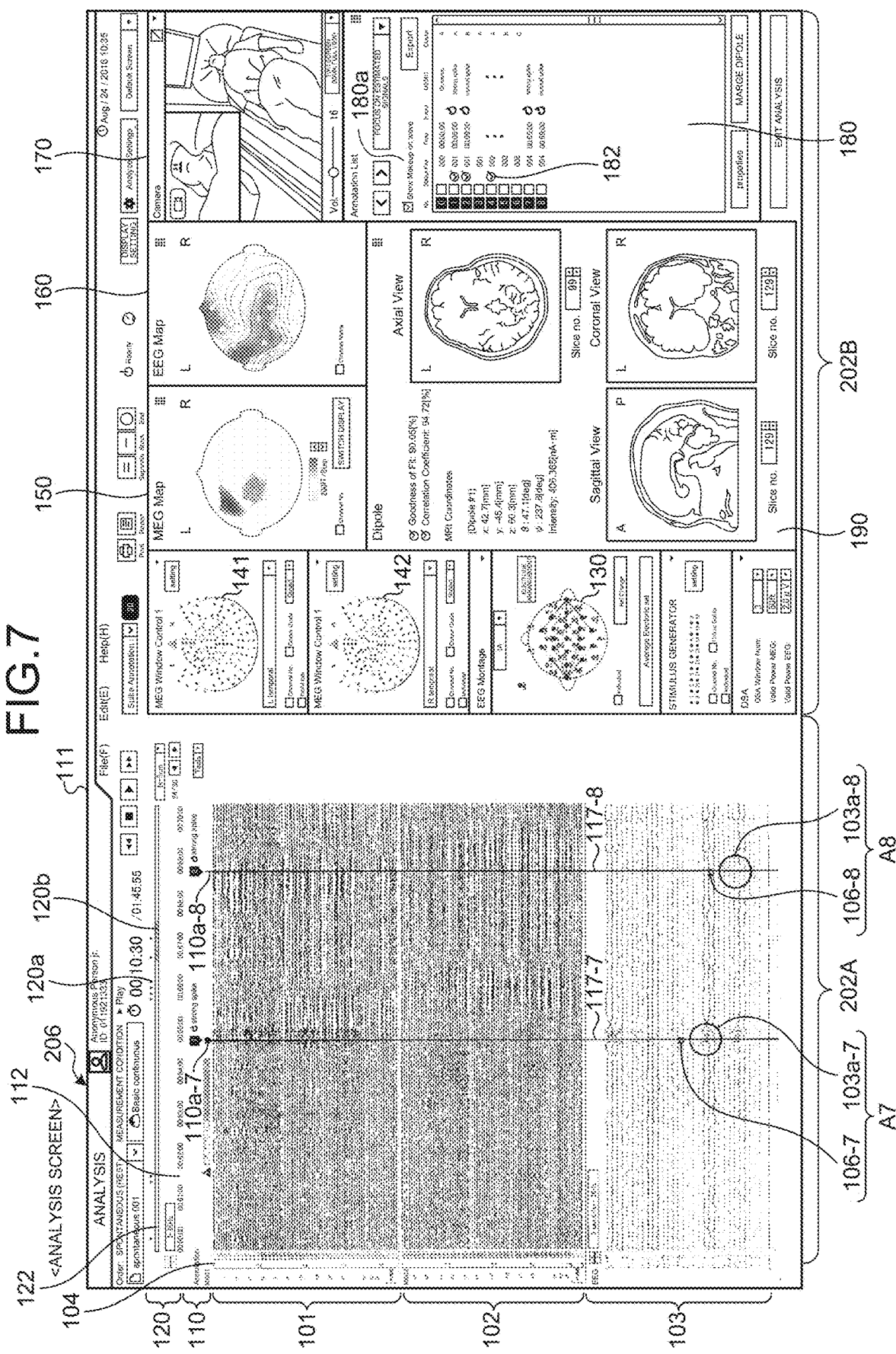
FIG. 7 is a diagram illustrating an example of an analysis screen.

FIG. 7 is a diagram illustrating an example of an analysis screen 206 displayed in the information processing apparatus 50 at the time of analysis. The analysis screen 206 is displayed when an "analysis" button is selected in the start screen 204 illustrated in FIG. 4. The analysis screen 206 is a screen in which biological data indicating a temporal change of one or more biological signals of a subject measured by measurement (in this example, magnetoencephalography signals that are obtained from a group of magnetic sensors corresponding to the right side of the head of the to-be-measured person, magnetoencephalography signals that are obtained from a group of magnetic sensors corresponding to the left side of the head of the to-be-measured person, and electroencephalography signals that are obtained from electrodes for electroencephalography measurement on the to-be-measured person) is associated with one or more annotations that are with respect to the biological data at the time of measurement. The information processing apparatus 50 of the present embodiment has a function to control display of the analysis screen 206 on a display unit (the display device 26 as described above). In the example illustrated in FIG. 7, the analysis screen 206 includes a region 202A for displaying waveforms (corresponding to the biological data) indicating temporal changes of three recorded biological signals together with annotations, and a region 202B for displaying analysis information. In this example, the waveforms indicating temporal changes of the three recorded biological signals are displayed in the analysis screen 206, but the number of signals is not limited to three because an input signal of the stimulator 20 may be displayed in some cases. The region 202A for displaying the recorded signal waveforms and the annotation information is arranged on the left side of the screen when viewed from the measurer's side, and the region 202B for displaying analysis is arranged on the right side when viewed from the measurer's side. This is because this configuration can improve operation efficiency for checking or confirming an analysis result in the region 202B by operating a mouse or the like while checking or selecting a signal waveform in the region 202A at the time of analysis.

In this example, the waveforms of the magnetoencephalography signals in the waveform display regions 101 and 102 are displayed above a screen of the waveforms of the electroencephalography signals in the waveform display region 103 of the region 202A. Further, in the region 202B arranged on the right side of the region 202A, the magnetoencephalography distribution maps 141 and 142 are displayed in a screen region that is near the region 202A and on the upper part of the screen, and the electroencephalography distribution map 130 is displayed below the magnetoencephalography distribution maps 141 and 142. Therefore, the analyzer is able to move the line of sight in order of "the waveforms of the electroencephalography signals" in the waveform display region 103, "waveforms of the magnetoencephalography signals" in the waveform display regions 101 and 102, the magnetoencephalography distribution maps 141 and 142, and the electroencephalography distribution map 130 (clockwise in this example). Consequently, the analyzer (or the measurer) can efficiently move the line of sight, so that it is possible to improve the analysis operation efficiency. Meanwhile, while it is explained that the line of sight moves clockwise in the example described above, embodiments are not limited to this example.

The region 202A includes the first display region 110 and a second display region 120 for displaying time information at the time of measurement in the horizontal direction (first direction) of the screen, and includes the waveform display regions 101 to 103 for displaying different kinds of recorded signal waveforms in parallel in the vertical direction (second direction) of the screen.

The time axis 112 that indicates a lapse of time at the time of recording and annotations 110*a*-7 and 110*a*-8 that are added along the time axis 112 are displayed in the first display region 110. A time axis 122 that displays the entire recording time is displayed in the second display region 120. A pointer mark 120a indicating a temporal position at which an annotation is added and a time zone 120b indicating a time zone in which signal waveforms that are currently displayed in the waveform display regions 101 to 103 are recorded are displayed along the time axis 122. With this display, the analyzer is able to intuitively recognize a timing at which a currently-analyzed signal waveform is acquired during measurement and recording.

The analyzer is able to display signal waveforms corresponding to a desired time zone in the waveform display regions 101 to 103 by, for example, dragging the time zone 120b on the time axis 122 after opening the analysis screen. Alternatively, as will be described later, by selecting a desired annotation from the annotation list 180, it is possible to display signal waveforms that are present at and around the annotation in the waveform display regions 101 to 103.

The waveform display regions 101 to 103 display annotations A7 and A8 that are added to the signal waveforms at the time of recording. Marks 103a-7 and 103a-8 are displayed in a highlighted manner, and corresponding attribute icons 106-7 and 106-8 are displayed near the marks 103a-7 and 103a-8. Further, vertical lines 117-7 and 117-8 indicating temporal positions of the marks 103a-7 and 103a-8 are displayed. With the display of lines 117, when an annotation is added in association with specification of a predetermined portion in the waveform display region 103 for example, it is possible to easily view the specification result even in the waveform display regions 102 and 101 that are display areas for different kinds of signals. The lines 117 may be included in the annotation information because they make it possible to easily view the annotation information, and therefore may be referred to as "annotation lines".

The analysis screen 206 illustrated in FIG. 7 displays the magnetoencephalography distribution maps 141 and 142 corresponding to the signal waveforms that are displayed in the waveform display regions 101 and 102, and displays the electroencephalography distribution map 130 corresponding to the signal waveforms that are displayed in the waveform display region 103. Further, an isofield contour map 150 of a magnetoencephalography (MEG), a map area 160 of an electroencephalography (EEG), and a display window 190 for a tomography image that is acquired by magnetic resonance imaging (MRI) of the brain of the to-be-measured person are displayed. In the isofield contour map 150, a spring region and a sucking region of a magnetic field are displayed in different colors, so that it is possible to visually recognize a direction of the flow of electrical current. The isofield contour map 150 and the map area 160 are information that are obtained after measurement is completed, and the MRI tomography image is information that is separately obtained through an examination.

A video of the to-be-measured person at the time of measurement is displayed in the monitor window 170 in synchronization with times at which the signal waveforms in the waveform display regions 101 to 103 are obtained. The analyzer is able to analyze the signal waveforms while checking the condition of the to-be-measured person by viewing the monitor window 170.

The annotation list 180 contains a list of all of annotations that are added during the measurement and recording. By clicking a desired annotation number 181 or a desired row, it is possible to display, in the waveform display regions 101 to 103 illustrated in FIG. 7, signal waveforms corresponding to a predetermined time zone including the temporal position to which the annotation is added.

An estimation completion mark 182 is displayed with respect to an annotation, for which the analyzer has estimated a final signal source by checking the signal waveform corresponding to the annotation portion, unlike the measurement recording screen 205.

Figure 8:
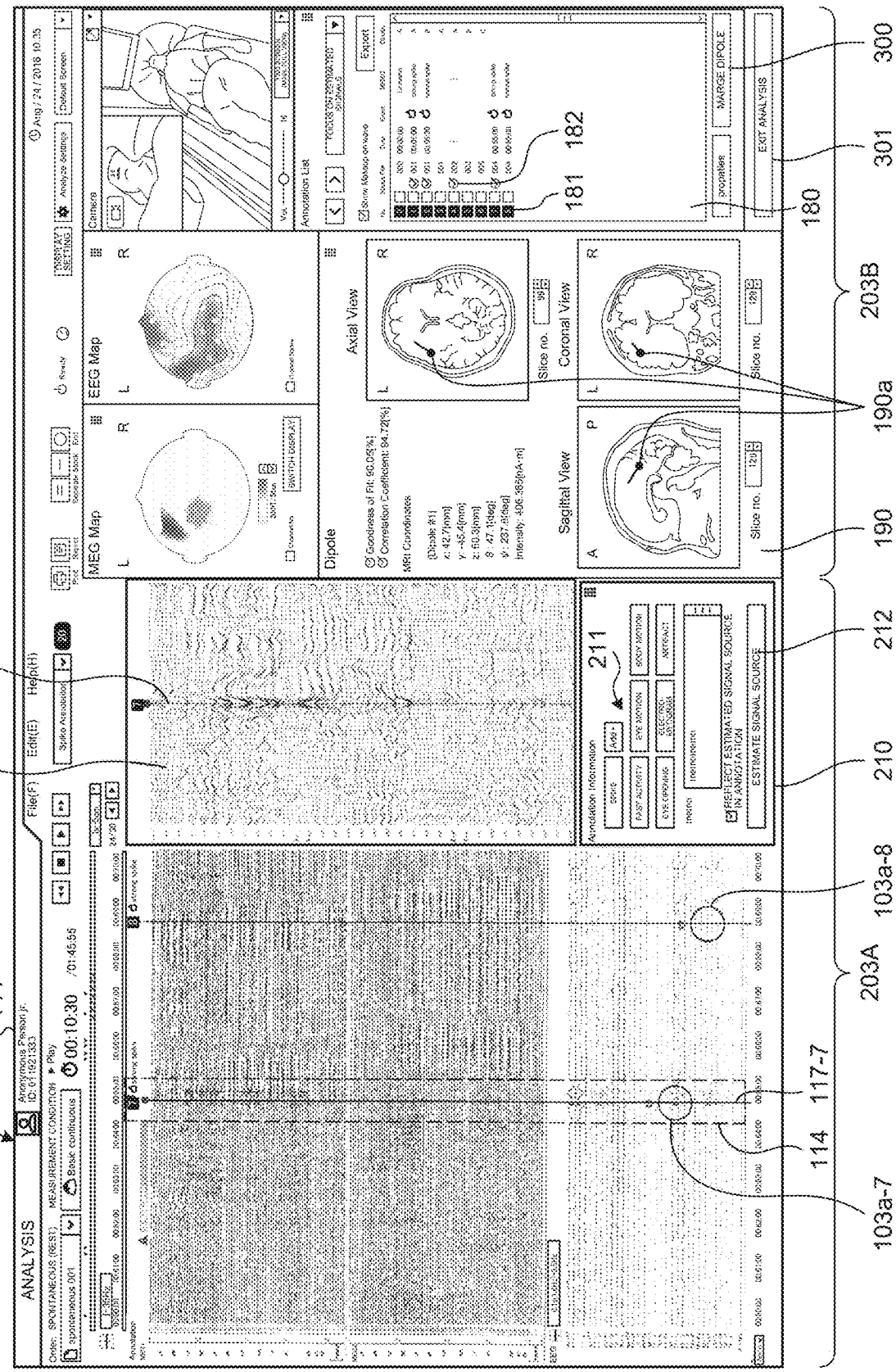
FIG. 8 is a diagram illustrating a screen that is displayed after a specific annotation line is selected in the screen illustrated in FIG. 7.

FIG. 8 is a diagram illustrating a screen that is displayed after a specific annotation line is selected in the screen illustrated in FIG. 7. FIG. 8 illustrates an entire screen that is displayed immediately after the line 117-7 is selected (for example, double clicked) in the analysis screen 206 illustrated in FIG. 7. When the analyzer focuses attention on the annotation A7 and selects (for example, double clicks) the line 117-7 to analyze waveforms in this region, signal waveforms near the highlighted signal waveforms are displayed in an enlarged manner in an enlarged display region 200 as illustrated in FIG. 8. The signal waveforms are displayed in an enlarged manner over a certain time range indicated in a region 114, together with a line 217-7 that indicates a temporal position.

By displaying the enlarged views of the signal waveforms in the enlarged display region 200, the analyzer is able to reconfirm the validity of the mark that is added at the time of recording or check waveform portions that have not been checked during measurement and recording. For example, by dragging the line 217-7 to the left or right, it is possible to identify or change an accurate portion of a problematic waveform.

It may be possible to specify a type of signal waveforms and a channel range to be displayed in the enlarged display region 200. For example, the analyzer moves the line of sight from the mark 103a-7 that is highlighted in the waveform display region 103 to the upper part of the screen and checks whether a singularity of amplitude is present in the waveforms displayed in any of the waveform display regions 101 and 102 of magnetoencephalography waveforms. In this case, it is possible to display enlarged views of magnetoencephalography waveforms related to the mark 103a-7 in the enlarged display region 200 by specifying a target channel region of the waveform display region 101 or the waveform display region 102.

A confirmation window 210 is displayed below the screen of the enlarged display region 200. The confirmation window 210 includes signal waveform attribute buttons 211 and an estimation button 212 for a signal source. The attribute buttons 211 correspond to pieces of attribute information that are included in the pop-up window 115 of the measurement recording screen 205, and it is possible to select any of the attribute buttons 211 to select a correct attribute when an attribute that is added at the time of recording is wrong. If a correct position and/or selection of an attribute of the signal waveform are/is confirmed, it is possible to reflect estimation of a signal source in the annotation by clicking the estimation button 212. In other words, the information processing apparatus 50 of the present embodiment has a function to estimate a signal source corresponding to an annotation that is selected from the analysis screen 206. The estimated signal source is displayed, in a superimposed manner, on a tomography image that corresponds to the estimated signal source among a plurality of MRI-based tomography images of the brain of the to-be-measured person.

When the signal waveform position and/or the attribute for a desired annotation are/is confirmed and the signal source estimation button 212 is selected in FIG. 8, the estimation completion mark 182 is added to a corresponding annotation in the annotation list 180. Further, dipole estimation results 190*a* are displayed in MRI tomography images in the display window 190.

Figure 9:
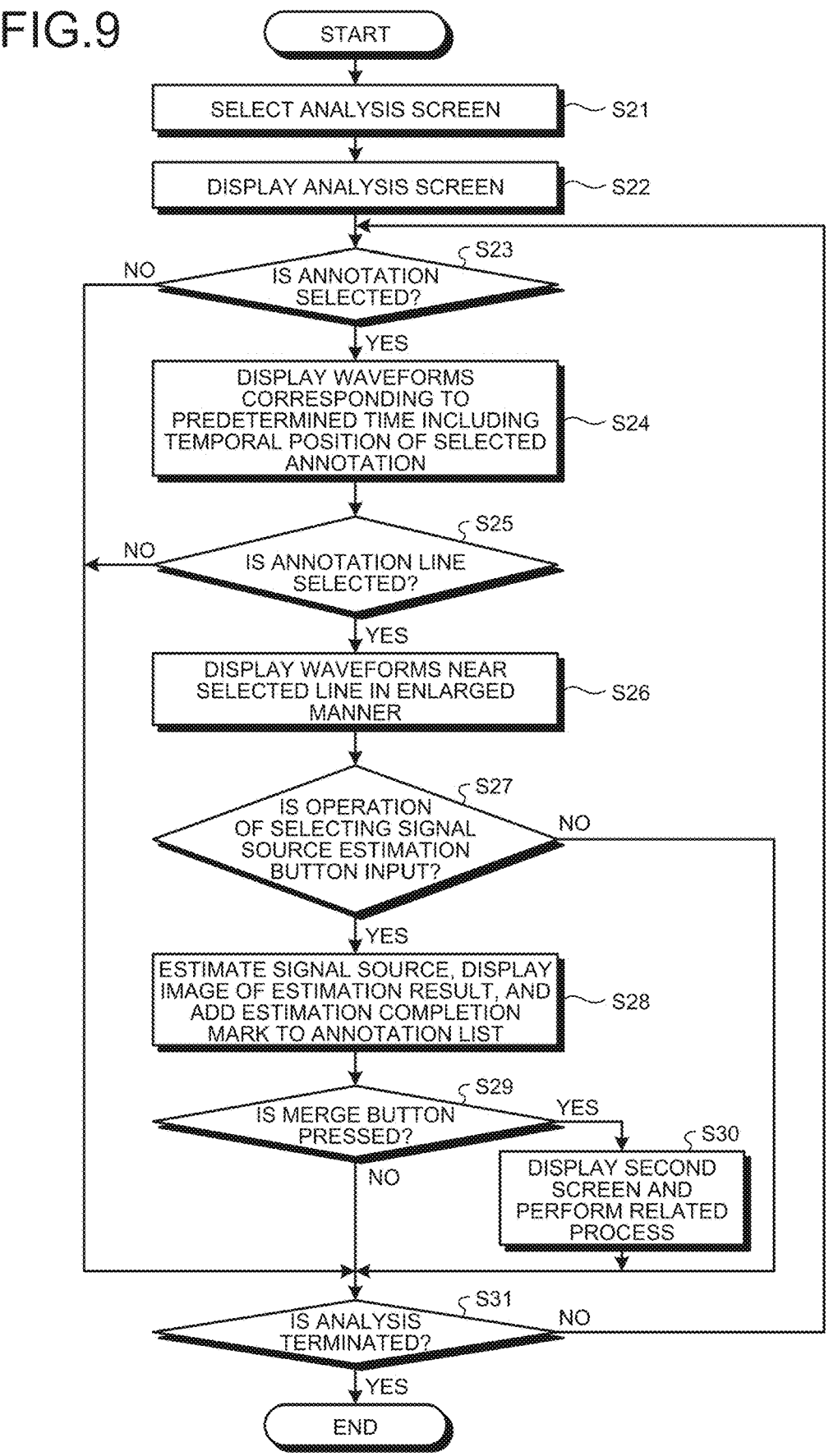
FIG. 9 is a flowchart illustrating the flow of an information display process at the time of analysis.

FIG. 9 is a flowchart illustrating the flow of an information display process that is performed by the information processing apparatus 50 at the time of analysis. When "analysis" is selected in the start screen 204 (see FIG. 4) (Step S21), analysis is started and the analysis screen 206 is displayed (Step S22). The analysis screen 206 at the initial time may be a blank screen in which no signal waveform is displayed or may display signal waveforms in a certain time range at the beginning or end of the recording. When the analysis screen 206 is displayed, it is determined whether a specific annotation is selected (Step S23). The annotation may be selected by selecting a specific annotation number or a specific row in the annotation list 180 or by specifying a temporal position by operating the time zone 120*b* on the time axis 122 in the second display region 120. If an annotation is selected (YES at Step S23), signal waveforms corresponding to a predetermined time including the temporal position of the selected annotation are displayed (Step S24).

In the displayed screen, it is determined whether the line 117 indicating a temporal position of a mark displayed in a highlighted manner is selected (Step S25). If the line 117 is selected (YES at Step S25), signal waveforms in a certain time range including the selected line are displayed in an enlarged manner as illustrated in FIG. 8 (Step S26). It is not always necessary to display enlarged views of signal waveforms that are present near the mark being displayed in a highlighted manner, but it may be possible to display enlarged views of signal waveforms of a different kind that are present at the same temporal position. For example, when a mark displayed in a highlighted manner is added to electroencephalography signal waveforms, it may be possible to display enlarged views of magnetoencephalography signal waveforms that are present at the same temporal position. Further, it may be possible to display enlarged views of signal waveforms that are acquired by channels in a certain range including a channel that has acquired the marked signal waveform, instead of displaying enlarged views of signal waveforms of all of the channels. In this case, it may be possible to determine a type of signal waveforms to be displayed in an enlarged manner and/or determine whether designation of a channel range is input or not.

Subsequently, it is determined whether the signal source estimation button 212 illustrated in FIG. 8 is pressed (Step S27). If the signal source estimation button 212 is pressed (YES at Step S27), calculation for estimating a signal source is performed. The estimation result 190*a* is displayed on an MRI tomography screen of the display window 190 and the estimation completion mark 182 is added to the annotation list 180 (Step S28). Then, if operation of pressing a merge button 185 that is arranged below the annotation list 180 is received (YES at Step S29), the information processing apparatus 50 displays a different screen and performs a process related to the different screen (Step S30). If operation of pressing the merge button 185 is not received (NO at Step S29), or after S30, it is determined whether operation of pressing an analysis termination button 301 is received (Step S31). If an annotation is not selected (NO at Step S23), if an annotation line for displaying an enlarged view is not selected (NO at Step S25), or if operation of inputting a selection of the signal source estimation button is not received (NO at Step S27), the process proceeds to Step S31 and it is determined whether to terminate the analysis. Steps S23 to S30 are repeated (NO at Step S31) until operation of pressing the analysis termination button 301 is received (YES at Step S31).

It may be possible to determine whether an annotation is changed between Step S26 and Step S27. If an annotation is changed, this change is reflected in the annotation list 180, and the process proceeds to the determination at Step S27.

Next, an analysis method using averaging will be described. A method of performing averaging on multiple signals and performing the above-described dipole estimation based on a result of the averaging to observe reaction to multiple stimuli has been known. In the following, an averaging process at the time of an analysis process that is one example of signal processing will be described below, but it may be possible to apply averaging at the time of a recording process that is another example of signal processing.

By performing the averaging process, it is possible to reduce amplitude of signals with different phases. In other words, it is possible to reduce noise, such as white noise. As a result, it is possible to more clearly find reaction (signals) to stimuli.

However, if an inappropriate factor is mixed in signals to be subjected to averaging, the factor becomes noise and may make subsequent analysis difficult.

For example, when reaction to visual stimuli is to be observed, and if averaging is performed on signals including signals that are obtained when a subject is sleeping (closing eyes), the signals become noise signals and have a negative effect on the averaging because the signals do not represent reaction to the visual stimuli.

A case will be described below in which reaction to visual stimuli is measured, for simplicity of explanation. Further, a case will be described in which sleep is detected as the cerebral status of the subject.

Various methods of detecting sleep have been proposed. In this example, it is possible to use any method as long as activity within the brain is not affected. For example, it may be possible to use a method described in Japanese Patent Application Laid-open No. 2016-87072. This method is explained based on a case using EEG, but the method can be adopted to MEG signals in the same manner.

Figure 10:
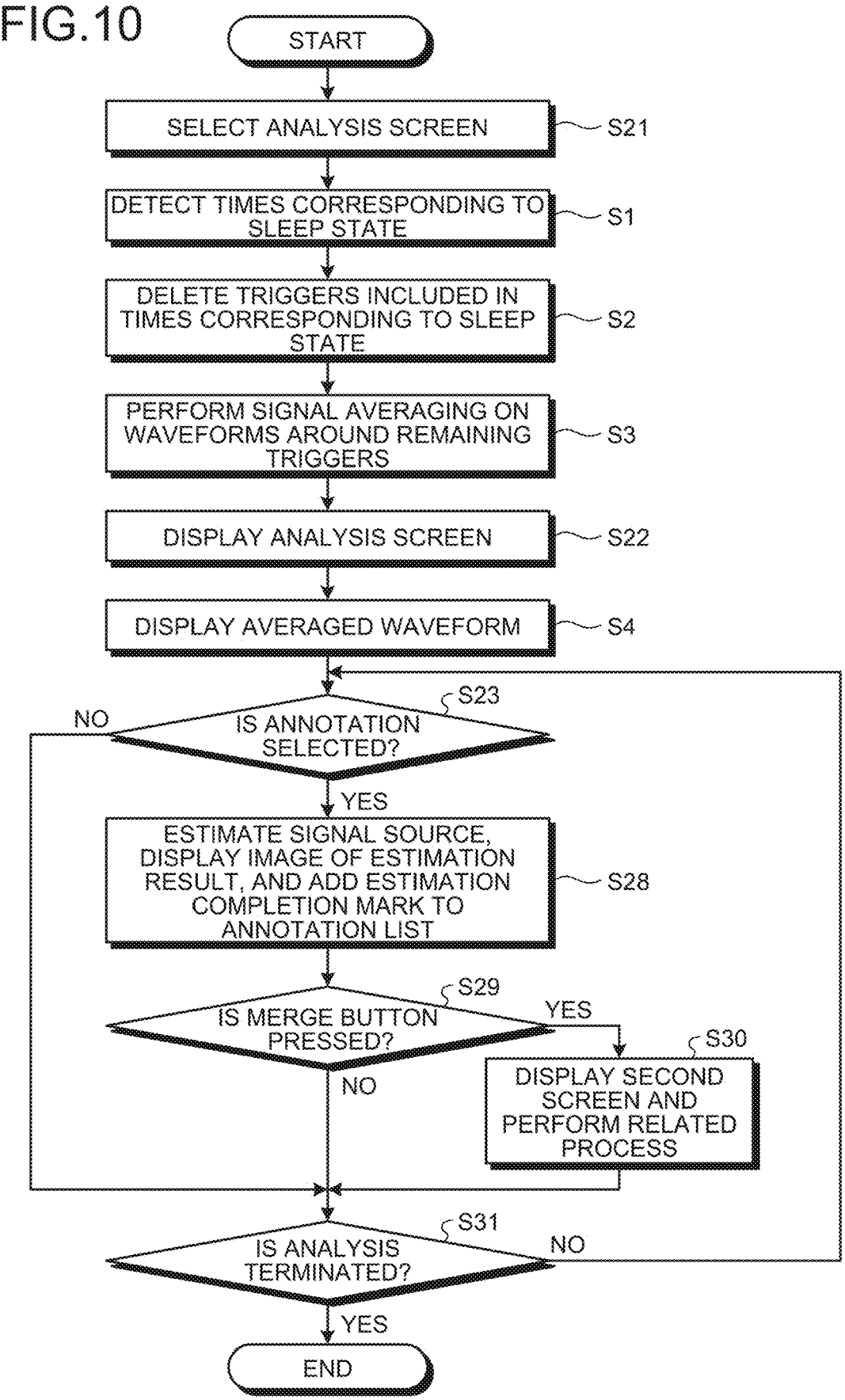
FIG. 10 is a flowchart schematically illustrating the flow of an information display process that is performed using averaging at the time of analysis.

FIG. 10 is a flowchart schematically illustrating the flow of an information display process that is performed using averaging at the time of analysis. The flow of the process will be described below based on FIG. 10 and FIG. 3.

An evoking signal is stored in the recording/analysis information storage unit 254 via the sensor information acquiring unit 253. Similarly, a trigger is stored in the recording/analysis information storage unit 254 via the trigger information acquiring unit 256. When each data is stored, the analyzing unit 252 performs an averaging process.

As illustrated in FIG. 10, when "analysis" is selected in the start screen 204 (see FIG. 4) (Step S21), the information processing apparatus 50 proceeds to Step S1.

The analyzing unit 252 detects times corresponding to a sleep state (Step S1). The analyzing unit 252 detects the sleep state and the times corresponding to the sleep state by applying, for example, the method described in Japanese Patent Application Laid-open No. 2016-87072 to the sensor information. In this case, it is determined that a sleep detection signal is detected (ON) when alpha waves subjected to frequency analysis account for less than 50% of the epoch, and the sleep detection signal is stored in the recording/analysis information storage unit 254.

Subsequently, the analyzing unit 252 deletes triggers that are included in the times corresponding to the sleep state (Step S2). More specifically, the analyzing unit 252 extracts trigger information from the recording/analysis information storage unit 254, deletes triggers that are included in a range in which the above-described sleep detection signal is ON, and store remaining triggers in the recording/analysis information storage unit 254. In the present embodiment, the "triggers" are trigger signals (stimulus generating signals) indicating times at which stimuli are generated.

Subsequently, the analyzing unit 252 performs averaging on waveforms that are present around the remaining triggers (Step S3). More specifically, the analyzing unit 252 calls the trigger information again from the recording/analysis information storage unit 254, and generates an averaged waveform by extracting times around the triggers. The generated averaged waveform is stored in the recording/analysis information storage unit 254.

Specifically, the analyzing unit 252 extracts signals between/within a prior time Tpr (milliseconds (ms)) that is prior to a trigger and a posterior time Tpo (ms) that is posterior to the trigger, and performs averaging on the extracted signals. With this operation, it is possible to obtain an average signal between −Tpr to Tpo. In the present embodiment, the "signal" is a signal used for dipole estimation and therefore is basically an MEG signal, but it may be possible to use an EEG signal.

Thereafter, the analyzing unit 252 starts analysis and displays the analysis screen 206 (Step S22), and displays the averaged waveform (Step S4).

Figure 11:
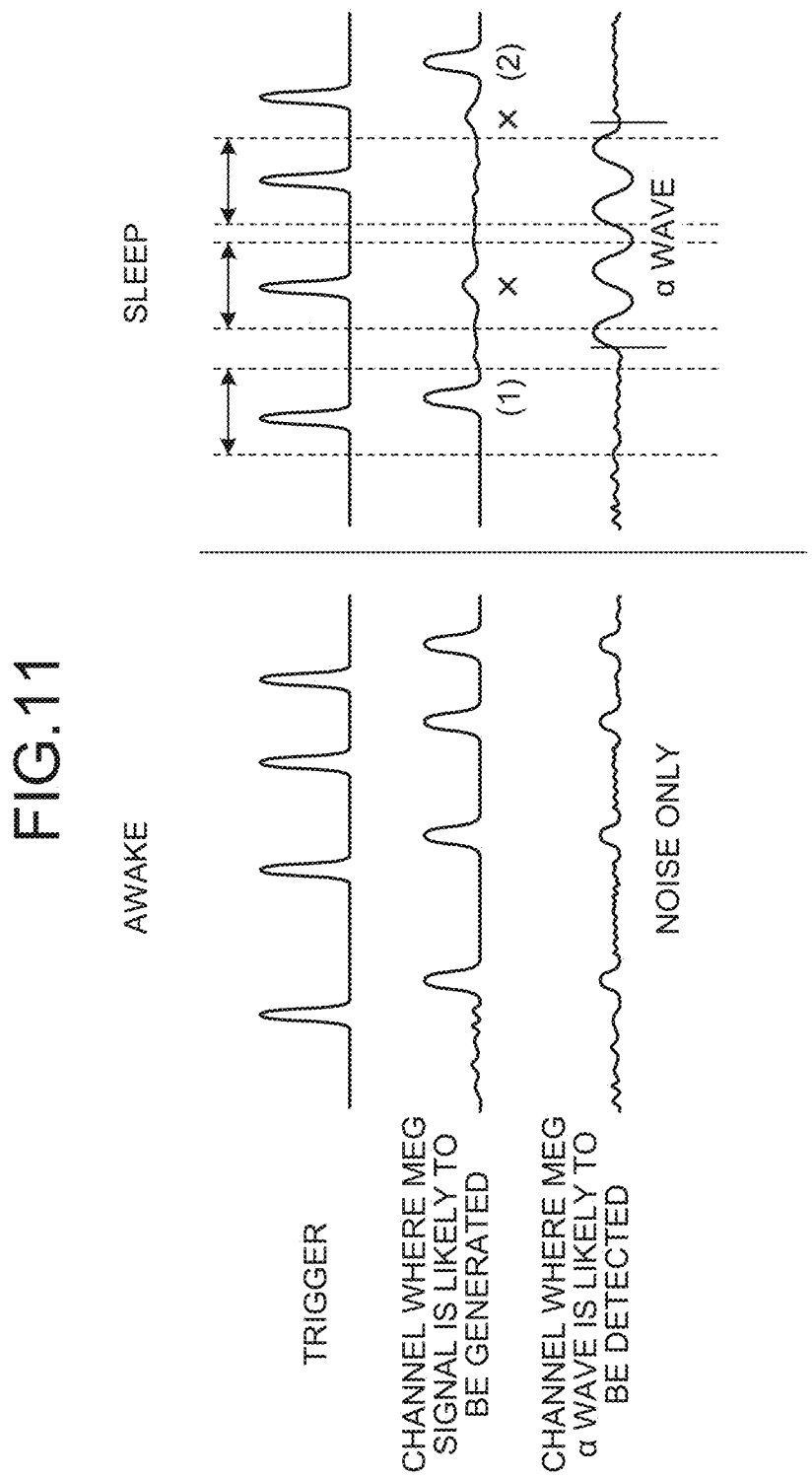
FIG. 11 is a diagram illustrating a display example of an averaged waveform.

The averaged waveform is used for various kinds of processing, similarly to a normal waveform. FIG. 11 is a diagram illustrating a display example of the averaged waveform. As illustrated in FIG. 11, when reaction to a visual stimulus is observed, triggers included in times in which the subject is in the sleep state are deleted, and averaging is performed on waveforms around the remaining triggers.

Referring back to FIG. 10, subsequent processes (addition of an annotation to dipole estimation) are performed in the same manner as in the case of a normal signal.

When the analysis screen 206 is displayed, it is determined whether a specific annotation is selected (Step S23). The annotation may be selected by selecting a specific annotation number or a specific row in the annotation list 180 or by specifying a temporal position by operating the time zone 120b on the time axis 122 in the second display region 120. If an annotation is selected (YES at Step S23), the process proceeds to Step S28.

At Step S28, the estimation result 190a is displayed on an MRI tomography screen of the display window 190 and the estimation completion mark 182 is added to the annotation list 180. Then, if operation of pressing the merge button 185 that is arranged below the annotation list 180 is received (YES at Step S29), the information processing apparatus 50 displays a different screen and performs a process related to the different screen (S30). If operation of pressing the merge button 185 is not received (NO at Step S29), or after S30, it is determined whether operation of pressing the analysis termination button 301 is received (Step S31).

If an annotation is not selected (NO at Step S23), the process proceeds to Step S31 and it is determined whether to terminate the analysis. Steps S23 to S30 are repeated (NO at Step S31) until operation of pressing the analysis termination button 301 is received (YES at Step S31).

The method described herein is one example, and methods of applying different stimuli and detecting different states have also been known. The method of detecting sleep can be applied in the same manner when reaction to other stimuli is to be observed. Further, it may be useful to detect extraordinary excitement/tension other than sleep, and remove corresponding data from analysis data.

While operation at the time of analysis has been described above, it may be possible to perform the same operation at the time of recording. When the operation is performed at the time of recording, similarly to the operation at the time of analysis, it is sufficient to detect the sleep detection signal and remove triggers that occurred at detected times from trigger data to be stored. Alternatively, it may be possible to separately record times as error trigger data and neglect the error triggers when performing averaging during analysis.

Further, when sleep is to be detected at the time of recording, and if the sleep detection signal occurs, it may be possible to suspend the measurement and allow the subject to get himself/herself in better physical condition. In this case, it is important to display occurrence of the sleep detection signal such that the occurrence can be easily recognized on the screen used for the recording.

Figure 12:
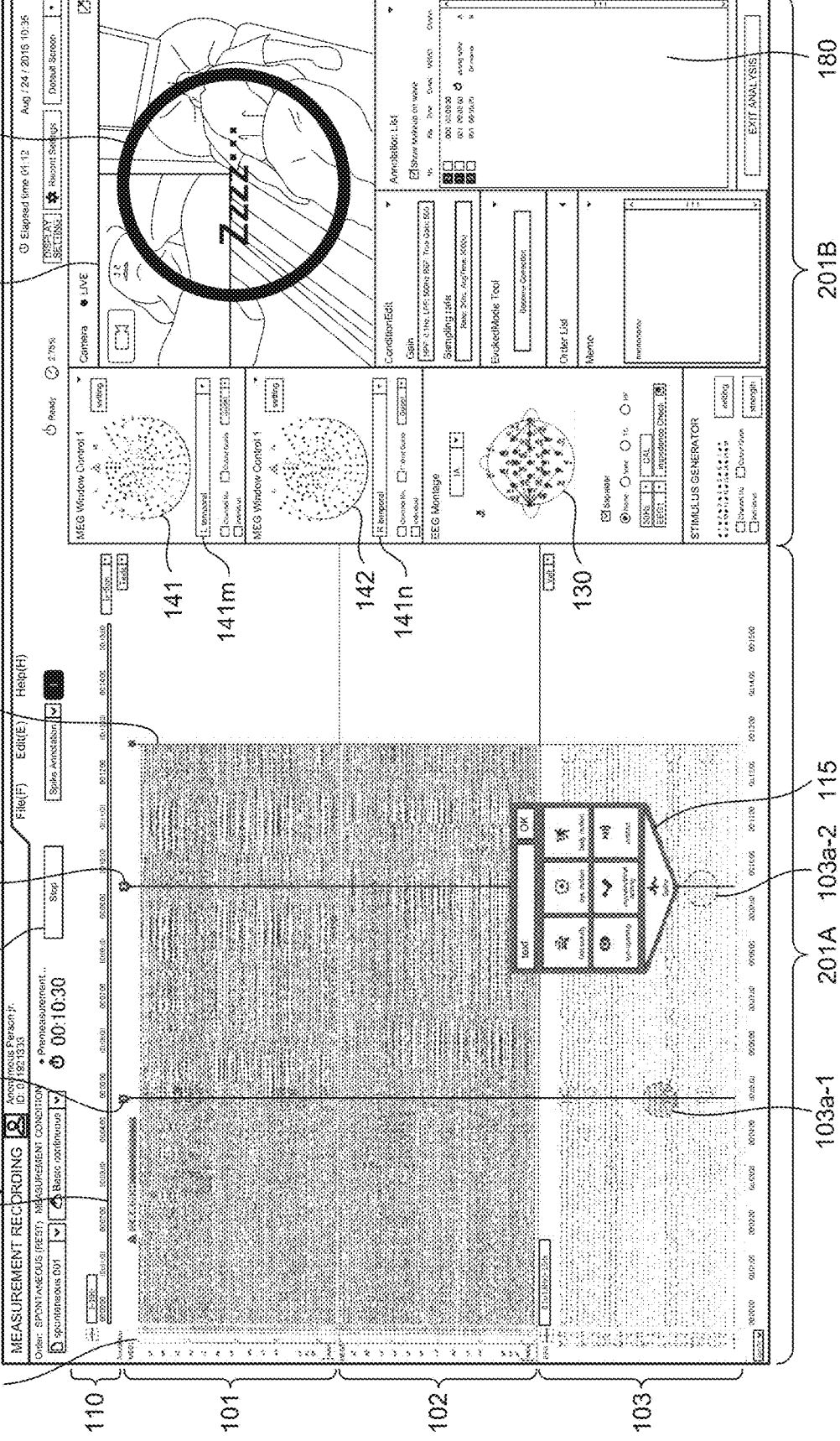
FIG. 12 is a diagram illustrating an example in which occurrence of a sleep detection signal is displayed in the measurement recording screen.

FIG. 12 is a diagram illustrating an example in which occurrence of the sleep detection signal is displayed in the measurement recording screen. As illustrated in FIG. 12, display 171 indicating occurrence of the signal detection signal is displayed on the monitor window 170 in the region 201B of the measurement recording screen 205.

FIG. 13 is a diagram illustrating standard sleep stages. FIG. 13 illustrates a table disclosed in "http://naraamt.or.jp/Academic/kensyuukai/2005/kirei/nouha_suimin/nouha-_suimin.html". In the present embodiment, it is assumed that the sleep detection signal is detected when alpha waves account for less than 50% of the epoch, but embodiments are not limited to this example. It may be possible to determine a sleep state on the basis of the standard sleep stages as illustrated in FIG. 13.

An example in which averaging is not associated will be described below.

When alpha waves are strong (in the sleep state or near-sleep state), it is possible to easily find epilepsy spike. Therefore, it is useful to measure the cerebral status at the strengths of alpha waves and preferentially display signals that are present in a time zone in which alpha waves are strong to an operator in order to easily find spike waveforms.

It is possible to adopt various display methods. For example, it may be possible to adopt a method of displaying only signals that are present in a time zone in which alpha waves have strengths larger than a certain value, or a method of changing display/background colors of signals that are present in a time zone in which alpha waves have strengths larger than a certain value.

FIG. 14 is a diagram illustrating another example of the analysis screen. As illustrated in FIG. 14, in the analysis screen 206, two-thirds of the right side of the MEG signals displayed in the waveform display regions 101 and 102 of the region 202A are regions in which alpha waves are strong. In the example illustrated in FIG. 14, the display control unit 251 changes display colors of the regions in which alpha waves are strong to darker colors than colors of the other regions so that the signals can be clearly viewed, on the basis of a result of frequency analysis performed on the biological signals.

As described above, according to the present embodiment, when measurement data with respect to multiple stimuli is to be analyzed, the cerebral status (the cerebral status, such as sleep, irrelevant to stimuli) is recognized by a non-invasive method, and measurement data with respect to stimuli that are applied in an inappropriate state is excluded from analysis targets, in other words, only measurement data that is obtained in an appropriate state is used as an analysis target, so that it is possible to improve analysis accuracy.

Further, a program executed by the biological signal measurement system 1 of the above-described embodiment may be provided by being recorded in a computer-readable recording medium, such as a compact disc ROM (CD-ROM), a flexible disk (FD), a compact disc recordable (CD-R), a digital versatile disk (DVD), or a universal serial bus (USB), in a computer-installable or computer-executable file format, or may be provided or distributed via a network, such as the Internet. Furthermore, various programs may be provided by being incorporated in a ROM or the like in advance.

According to an embodiment of the present invention, it is possible to improve analysis accuracy.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, nonvolatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. A biological signal analysis device comprising:
   memory having computer readable instructions stored thereon; and
   processing circuitry configured to execute the computer readable instructions to cause the biological signal analysis device to,
   acquire a plurality of biological signals of a measurement target from a biological signal measurement device configured to measure the plurality of biological signals;
   acquire, from a stimulator device configured to apply stimuli to the measurement target, trigger information indicating times at which the stimuli are generated; and
   process the plurality of biological signals, the processing the plurality of biological signals including,
      calculating biological information on the measurement target based on the plurality of biological signals,
      maintaining first pieces of the trigger information corresponding to times at which the plurality of biological signals correspond to an awake state of the measurement target, from the calculated biological information,
      deleting second pieces of trigger information corresponding to times at which the plurality of biological signals correspond to a sleep state of the measurement target, and
      generating an averaged waveform by performing an averaging process on the plurality of biological signals corresponding to the awake state in synchronization with the stimuli based on the first pieces of trigger information.

2. The biological signal analysis device according to claim 1, wherein the processing circuitry is further configured to cause the biological signal analysis device to:
   perform frequency analysis on the plurality of biological signals of the awake state.

3. The biological signal analysis device according to claim 2, wherein
   the sleep state corresponds to at least one of a plurality of sleep states, the plurality of sleep states including a light sleep state, a slow-wave sleep state, a deep sleep state, and a REM sleep state; and
   the processing circuitry is further configured to cause the biological signal analysis device to delete the second pieces of trigger information included in a time corresponding to the sleep state of the measurement target.

4. The biological signal analysis device according to claim 1, wherein the processing circuitry is further configured to cause the biological signal analysis device to:
   control display of a screen based on a result of frequency analysis performed on the plurality of biological signals.

5. The biological signal analysis device according to claim 4, wherein the processing circuitry is further configured to cause the biological signal analysis device to change a display color of a region of the screen determined to correspond to a sleep state as a result of the frequency analysis performed on the plurality of biological signals, to a darker color than a color of another region of the screen.

6. A biological signal measurement system comprising:
   a biological signal measurement device configured to measure a plurality of biological signals of a measurement target; and
   a biological signal analysis device configured to, acquire a plurality of biological signals of the measurement target from the biological signal measurement device;

acquire, from a stimulator device configured to apply stimuli to the measurement target, trigger information indicating times at which the stimuli are generated; and process the plurality of biological signals, the processing the plurality of biological signals including, calculating biological information on the measurement target based on the plurality of biological signals, maintaining first pieces of the trigger information corresponding to times at which the plurality of biological signals correspond to an awake state of the measurement target, from the calculated biological information, deleting second pieces of trigger information corresponding to times at which the plurality of biological signals correspond to a sleep state of the measurement target, and generating an averaged waveform by performing an averaging process on the plurality of biological signals corresponding to the awake state in synchronization with the stimuli based on the first pieces of trigger information.

7. A non-transitory computer-readable medium including programmed instructions, which when executed by processing circuitry of a computer, cause the computer to:

acquire, from a stimulator device configured to apply stimuli to a measurement target, trigger information indicating times at which the stimuli are generated; and process a plurality of biological signals of the measurement target, the processing the plurality of biological signals including, calculating biological information on the measurement target based on the plurality of biological signals, maintaining first pieces of the trigger information corresponding to times at which the plurality of biological signals correspond to an awake state of the measurement target, from the calculated biological information, deleting second pieces of trigger information corresponding to times at which the plurality of biological signals correspond to a sleep state of the measurement target, and generating an averaged waveform by performing an averaging process on the plurality of biological signals corresponding to the awake state in synchronization with the stimuli based on the first pieces of trigger information.

8. The non-transitory computer-readable medium according to claim 7, wherein the awake state corresponds to at least one of a wakefulness state, and a relaxed wakefulness state.

9. The biological signal analysis device according to claim 1, wherein the awake state corresponds to at least one of wakefulness state, and a relaxed wakefulness state.

10. The biological signal analysis device according to claim 1, wherein the processing circuitry is further configured to cause the biological signal analysis device to:

detect whether the measurement target is in the sleep state based on the plurality of biological signals.

11. The biological signal analysis device according to claim 1, wherein the processing circuitry is further configured to cause the biological signal analysis device to:

generate a dipole estimation of the plurality of biological signals of the awake state in synchronization with the stimuli based on the first pieces of trigger information.

12. The biological signal analysis device according to claim 1, wherein the stimuli applied to the measurement target is visual stimuli.

13. The non-transitory computer-readable medium of claim 7, wherein the computer is further caused to:

perform frequency analysis on the plurality of biological signals of the awake state.

14. The non-transitory computer-readable medium of claim 7, wherein the sleep state corresponds to at least one of a plurality of sleep states, the plurality of sleep states including a light sleep state, slow-wave sleep state, a deep sleep state, and a REM sleep state; and the computer is further caused to, delete the second pieces of trigger information included in a time corresponding to the sleep state of the measurement target.

15. The non-transitory computer-readable medium of claim 7, wherein the computer is further caused to:

control display of a screen based on a result of frequency analysis performed on the plurality of biological signals.

16. The non-transitory computer-readable medium of claim 15, wherein the computer is further caused to:

change a display color of a region of the screen determined to correspond to a sleep state as a result of the frequency analysis performed on the plurality of biological signals, to a darker color than a color of another region of the screen.

17. The non-transitory computer-readable medium of claim 7, wherein the computer is further caused to:

detect whether the measurement target is in the sleep state based on the plurality of biological signals.

18. The non-transitory computer-readable medium of claim 7, wherein the computer is further caused to:

generate a dipole estimation of the plurality of biological signals of the awake state in synchronization with the stimuli based on the first pieces of trigger information.

* * * * *